(12) United States Patent
Shimada et al.

(10) Patent No.: US 7,626,327 B2
(45) Date of Patent: Dec. 1, 2009

(54) LIGHTING APPARATUS WITH FILTER

(75) Inventors: Junichi Shimada, Kyoto (JP); Yoichi Kawakami, Kusatsu (JP); Motokazu Yamada, Anan (JP)

(73) Assignee: Nichia Corporation, Tokushima (JP)

( * ) Notice: Subject to any disclaimer, the term of this patent is extended or adjusted under 35 U.S.C. 154(b) by 401 days.

(21) Appl. No.: 11/067,891

(22) Filed: Mar. 1, 2005

(65) Prior Publication Data

US 2005/0194876 A1 Sep. 8, 2005

(30) Foreign Application Priority Data

Mar. 5, 2004 (JP) ............... 2004/063181
Dec. 7, 2004 (JP) ............... 2004/354720

(51) Int. Cl.
*H01J 1/62* (2006.01)
(52) U.S. Cl. ...................... 313/501; 313/498
(58) Field of Classification Search ................ 313/110, 313/498–512
See application file for complete search history.

(56) References Cited

U.S. PATENT DOCUMENTS

| | | | | |
|---|---|---|---|---|
| 6,639,360 | B2 * | 10/2003 | Roberts et al. | 313/512 |
| 2003/0100837 | A1 * | 5/2003 | Lys et al. | 600/476 |
| 2003/0133292 | A1 * | 7/2003 | Mueller et al. | 362/231 |
| 2003/0227023 | A1 * | 12/2003 | Chang et al. | 257/89 |

FOREIGN PATENT DOCUMENTS

| | | |
|---|---|---|
| EP | 0 808 606 | 11/1997 |
| JP | 61-211955 | 9/1986 |
| JP | 63-26308 | 2/1988 |
| JP | 4-177317 | 6/1992 |
| JP | 10-52430 | 2/1998 |
| JP | 11-99127 | 4/1999 |
| JP | 11-216115 | 8/1999 |
| JP | 2001-185371 | 7/2001 |
| JP | 2002-125984 | 5/2002 |
| JP | 2002-150803 | 5/2002 |
| JP | 2002-514127 | 5/2002 |
| JP | 2002-329896 | 11/2002 |
| JP | 2003-107579 | 4/2003 |
| JP | 2003-249693 | 9/2003 |
| JP | 2003-264845 | 9/2003 |
| JP | 2003-339738 | 12/2003 |
| JP | 2005-058440 | 3/2005 |
| WO | 99/01696 | 1/1999 |

* cited by examiner

*Primary Examiner*—Anne M Hines
(74) *Attorney, Agent, or Firm*—Wenderoth, Lind & Ponack, L.L.P.

(57) ABSTRACT

A lighting apparatus which improves identification of living body tissues, and is suitable for medical lighting. In the lighting apparatus, the light output in a range of wavelength 525 to 590 nm is not greater than ⅕ of the light output in a range of wavelength 380 to 780 nm corresponding to visible light components. The peak wavelength of a blue or bluish green light component included in the output light is in a range of 430 to 520 nm, and the peak wavelength of a red light component is not less than 600 nm. A green light component has the peak in a range of wavelength 520 to 590 nm, its spectral half-value width is not greater than 70 nm, and the light amount of at least the green light component can be independently adjusted.

12 Claims, 13 Drawing Sheets

(a)

(b)

LIGHTING APPARATUS WITH FILTER

BACKGROUND OF THE INVENTION

1. Technical Field

The present invention relates to a lighting apparatus, a filter apparatus and an image display suitable medical application, particularly to, a lighting apparatus, a filter apparatus and an image display which improve identification of living body tissues.

2. Description of Related Art

As lighting used in the medical field and so on, a shadowless lamp or astral lamp which does not cast a shadow under the light is used in general. As such a shadowless lamp, a high luminance lamp such as xenon lamp, halogen lamp and metal halide lamp with color temperature near sunlight is used (for example, Japanese Patent Laid-Open Publication TOKUKAI No. 2003-339738). However, it is important not only to provide shadowless effect but also easy identification of living body tissues for medical lighting. That is, it is desirable that the spectrum components of reflected light provide the component with heightened contrast of living body tissues. For example, a light source which provides sufficient color difference to identify an artery and a vein during an operation is required in a medical application.

On the other hand, in recent years, dissimilarly to an electric bulb such as an incandescent lamp which emits light with heat energy by heating the metal filament to the incandescence state with an electric current applied thereto, a lighting apparatus which employs a semiconductor light emitting element transforming electrical energy into electromagnetic radiation by using a semiconductor, or a light emitting device converting wavelength of light emitted from such a semiconductor light emitting element in combination with a phosphor has been developed. Particularly, a light emitting device using a nitride group semiconductor, such as gallium nitride, can emit ultraviolet light, blue light, green light, and soon. The device is high efficient and low power consumption, and in addition can be small, has resistance against mechanical vibration and so on, has a long life, and has high reliability. Since the device has these advantages, it is capable of being used in various applications. However, this type of semiconductor light emitting device generally has reflection spectrum components different from an electric bulb or sunlight. Accordingly, there is a problem that such a device is not suitable for a medical application. For example, when a white LED is used as medical lighting, it is difficult to identify an artery and a vein.

SUMMARY OF THE INVENTION

The present invention is aimed at solving the above-described problems. The object of the present invention is to provide a lighting apparatus, a filter apparatus, and an image display suitable for applications which require color discrimination of subject colors, such as improvement of identification of living body tissues for medical lighting.

To achieve the object, in a lighting apparatus according to a first aspect of the present invention, which can emit white light, the light output in a range of wavelength 525 to 590 nm is not greater than $1/5$ of the light output in a range of wavelength 380 to 780 nm corresponding to visible light components. Accordingly, spectrum components with large color difference are relatively emphasized. Therefore, it is possible to provide a lighting apparatus which improves identification of living body tissues, and is suitable for applications which require color discrimination of subject colors.

In a lighting apparatus according to a second aspect, the light output in the range of wavelength 525 to 590 nm can be not greater than $1/10$ of the light output in the range of wavelength 380 to 780 nm corresponding to visible light components. Accordingly, spectrum components with large color difference are relatively emphasized. Therefore, it is possible to provide a lighting apparatus which improves identification of living body tissues, and is suitable for applications which require color discrimination of subject colors.

In a lighting apparatus according to a third aspect, the peak wavelength of a blue or bluish green light component included in the output light can be in a range 430 to 520 nm. Accordingly, color difference of living body tissues can be emphasized with a blue or bluish green light component. Therefore, it is possible to provide a lighting apparatus which improves identification of living body tissues, and is suitable for applications which require color discrimination of subject colors.

In a lighting apparatus according to a fourth aspect, the peak wavelength of a blue or bluish green light component included in the output light can be in a range 480 to 510 nm. Accordingly, color difference of living body tissues can be emphasized with a blue or bluish green light component. Therefore, it is possible to provide a lighting apparatus which improves identification of living body tissues, and is suitable for applications which require color discrimination of subject colors.

In a lighting apparatus according to a fifth aspect, the peak wavelength of a red light component included in the output light can be not less than 600 nm. Accordingly, color difference of living body tissues can be emphasized with a red light component. Therefore, it is possible to provide a lighting apparatus which improves identification of living body tissues, and is suitable for applications which require color discrimination of subject colors.

In a lighting apparatus according to a sixth aspect, the peak wavelength of a red light component included in the output light can be in a range of 610 to 670 nm. Accordingly, the color difference of living body tissues can be emphasized with a red light component. Therefore, it is possible to provide a lighting apparatus which improves identification of living body tissues, and is suitable for applications which require color discrimination of subject colors.

In a lighting apparatus according to a seventh aspect, a green light component included in the output light can have the peak in a range of wavelength 520 to 590 nm, its spectral half-value width can be not greater than 70 nm, and the light amount of at least the green light component can be independently adjusted. Accordingly, in the case of a nervous tissue having lightness different from the other organ, the contrast between them can be emphasized. Therefore, it is possible to provide a lighting apparatus which improves identification of living body tissues, and is suitable for applications which require color discrimination of subject colors.

In a lighting apparatus according to an eighth aspect emitting light, a green light component included in the output light has the peak in a range of wavelength 520 to 590 nm, its spectral half-value width is not greater than 70 nm, and the light amount of at least the green light component can be independently adjusted. Accordingly, in the case of a nervous tissue having lightness different from the other organ, the contrast between them can be emphasized. Therefore, it is possible to provide a lighting apparatus which improves identification of living body tissues, and is suitable for applications which require color discrimination of subject colors.

In a lighting apparatus according to a ninth aspect, the apparatus can emit light containing only the green light component. Accordingly, the contrast of living body tissues can be emphasized only with monochromatic light containing only the green light component. Therefore, it is possible to provide a lighting apparatus which improves identification of living body tissues irrespective of lightness, and is suitable for applications which require color discrimination of subject colors.

In a filter apparatus transmitting light according to a tenth aspect, the amount of transmitted light in a range of wavelength 525 to 590 nm is not greater than ⅕ of the amount of transmitted light in a range of wavelength 380 to 780 nm corresponding to visible light components. Accordingly, spectrum components with large color difference are relatively emphasized. Therefore, it is possible to provide a filter apparatus which improves identification of living body tissues, and is suitable for applications which require color discrimination of subject colors.

In a filter apparatus according to an eleventh aspect, the amount of transmitted light in a range of wavelength 525 to 590 nm is not greater than ⅒ of the amount of transmitted light in a range of wavelength 380 to 780 nm corresponding to visible light components. Accordingly, spectrum components with large color difference are relatively emphasized. Therefore, it is possible to provide a filter apparatus which improves identification of living body tissues, and is suitable for applications which require color discrimination of subject colors.

In a filter apparatus according to a twelfth aspect, the peak wavelength of a blue or bluish green light component included in the transmitted light can be in a range of 430 to 520 nm. Accordingly, color difference of living body tissues can be emphasized with a blue or bluish green light component. Therefore, it is possible to provide a filter apparatus which improves identification of living body tissues, and is suitable for applications which require color discrimination of subject colors.

In a filter apparatus according to a thirteenth aspect, the peak wavelength of a blue or bluish green light component included in the transmitted light can be in a range of 480 to 510 nm. Accordingly, the color difference of living body tissues can be emphasized with a blue or bluish green light component. Therefore, it is possible to provide a filter apparatus which improves identification of living body tissues, and is suitable for applications which require color discrimination of subject colors.

In a filter apparatus according to a fourteenth aspect, the peak wavelength of a red light component included in the transmitted light can be not less than 600 nm. Accordingly, color difference of living body tissues can be emphasized with a red light component. Therefore, it is possible to provide a filter apparatus which improves identification of living body tissues, and is suitable for applications which require color discrimination of subject colors.

In a filter apparatus according to a fifteenth aspect, the peak wavelength of a red light component included in the transmitted light can be in a range of 610 to 670 nm. Accordingly, color difference of living body tissues can be emphasized with a red light component. Therefore, it is possible to provide a filter apparatus which improves identification of living body tissues, and is suitable for applications which require color discrimination of subject colors.

A filter apparatus transmitting light according to a sixteenth aspect, wherein the apparatus has a peak in the transmitted light components in a range of wavelength 520 to 590 nm, and a transmittance which is set such that the amount of transmitted light in this range is not less than ½ of the total amount of transmitted light in range of wavelength 380 to 780 nm corresponding to visible light components. Accordingly, in the case of a nervous tissue having lightness different from the other organ, the contrast between them can be emphasized. Therefore, it is possible to provide a filter apparatus which improves identification of living body tissues, and is suitable for applications which require color discrimination of subject colors.

In an image display according to a seventeenth aspect including video-image processing, the image output corresponding to a range of spectral wavelength 525 to 590 nm in the subject side is not greater than ⅕ of the image output corresponding to a range of spectral wavelength 380 to 780 nm in the subject side. Accordingly, spectrum components with large color difference are relatively emphasized. Therefore, it is possible to provide a filter apparatus which improves identification of living body tissues, and is suitable for applications which require color discrimination of subject colors.

In an image display according to an eighteenth aspect, the image output corresponding to a range of spectral wavelength 520 to 590 nm in the subject side can be not less than ½ of the image output corresponding to the range of spectral wavelength 380 to 780 nm in the subject side. Accordingly, in the case of a nervous tissue having lightness different from the other organ, the contrast between them can be emphasized. Therefore, it is possible to provide an image display which improves identification of living body tissues, and is suitable for applications which require color discrimination of subject colors.

According to a lighting apparatus, a filter apparatus and an image display apparatus of the present invention, it is possible to achieve excellent features that sufficient color difference in spectrum components of reflected light for prime living body tissues can be obtained, and they can be suitably used for applications which require color discrimination of subject colors. That is, when light source with high color temperature is used, color difference of organs with high reflectivities can be clear, and organs can be easily identified by reducing a spectrum component which provides difficulty in identification. In the case of a living body tissue having a large contrast difference from the other organ such as nervous tissue, the contrast of living body tissues can be improved by adjusting only a particular wavelength range. Accordingly, it is possible to easily identify different types of cells. Furthermore, according to the use of a similar principle, it is possible to provide not only a light source but also a filter apparatus which improves identification of living body tissues by adjusting spectrum components of transmitted light. Moreover, it is possible to provide an image display which can display an image in which identification of living body tissues is improved by applying electrical processing such as image processing according to a similar principle.

DETAILED DESCRIPTION OF THE PREFERRED EMBODIMENTS

Figure 1:
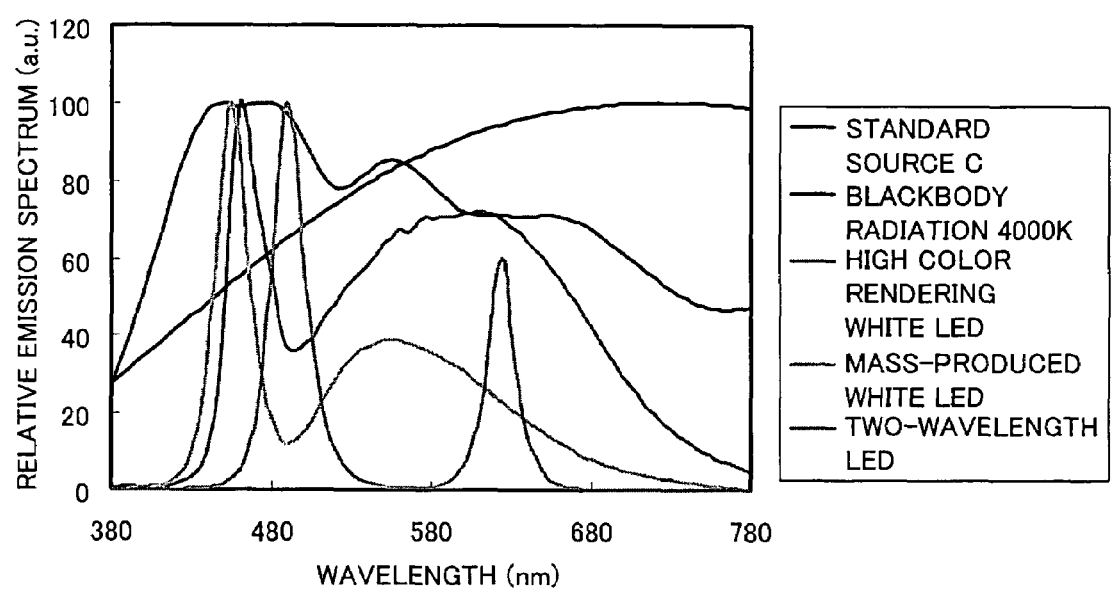
FIG. 1 is a graph showing an emission spectrum of each light source used in one embodiment of the present invention.

The following description will describe embodiments according to the present invention with reference to the drawings. It should be appreciated, however, that the embodiments described below are illustrations of a lighting apparatus, a filter apparatus, and an image display to give a concrete form to technical ideas of the invention, and a lighting apparatus, a filter apparatus, and an image display of the invention are not specifically limited to description below.

Furthermore, it should be appreciated that the members recited in the claims attached hereto are not specifically limited to members in the illustrated embodiments. Unless otherwise specified, any dimensions, materials, shapes and relative arrangements of the parts described in the embodiments are given as an example and not as a limitation. Additionally, the sizes and the arrangement relationships of the members in each of drawings are occasionally shown on an enlarged scale for ease of explanation. Members that are the same as or similar to those of this invention are attached with the same designation and the same reference numerals and their description is omitted. In addition, a plurality of structural elements of the present invention may be configured as a single part which serves the purpose of a plurality of elements; on the other hand, a single structural element may be configured as a plurality of parts which serve the purpose of a single element.

In order to obtain lighting and filter apparatuses, and an image display suitable for applications which require color discrimination of subject colors, such as medical applications, the inventors measured the reflection spectrums of living body tissues under various conditions, and finally found preferable characteristics. The reflection spectrums of the various living body tissues of a pig under general anesthesia as samples were measured in a living state. The color differences of tissues under various light sources were acquired based on the data, and the characteristics suitable for the light source were obtained. Accordingly, a filter apparatus and an image display with similar characteristics have been developed. Photonic Multichannel Spectral Analyzer PMA-11 of Hamamatsu Photonics K. K. was used for measurement of the reflection spectrum. As for the lighting source, a halogen lamp was used as a reference light source. The reflection spectrum of barium sulfate was used as reference light. The reflection spectrum of each tissue was acquired based on the difference between reflection spectrum of barium sulfate and the reflection spectrum of living body tissue in irradiation. Since blood is included in a living body tissue, the color of blood varies with the oxygen concentration in the blood. In the state where the color of blood does not vary, the inventors analyzed the spectrum of reflected light in the state where each tissue was alive. Accordingly, a subject tissue moved due to breathing or heartbeat. In addition, the state of its surface was wet and curved. Thus, its state was different from the state of barium sulfate surface as the reference. For this reason, it is considered that the measured value includes deviations to a certain extent.

Blackbody radiation light, a mass-produced white LED, a two-wavelength LED, a second two-wavelength LED, an LED with peak wavelength near 555 nm were used as light sources, and the reflection spectrums of a vein, arterial blood, a liver, and a lung were measured, respectively. Blackbody radiation light had color-temperature of 4000K, and characteristics near a conventional light source for a shadowless lamp and so on used in an operating room. The mass-produced white LED was a combination of blue LED (peak wavelength of about 450 nm), and a YAG phosphor. The phosphor emitted yellow group light. The phosphor was dispersed in mold resin which molded the LED. The phosphor absorbed a part of blue light from LED, and emitted yellow light by converting the wavelength of the blue light. A color mixture of blue light and yellow light allows white group light emission. The two-wavelength LED was a combination of a blue green light component and a red light component. In this embodiment, a blue LED with a peak wavelength of about 490 nm and a red LED with a peak wavelength of about 625 nm were combined and used. In the second two-wavelength LED, a blue LED with a peak wavelength of about 490 nm and a red LED with a peak wavelength of about 650 nm were combined and used. Standard source C as the reference light was an artificial light source with correlated color temperature of about 6774 K obtained by combination of a predetermined filter and standard source A. As a valuation method of measured data, various calculation methods have been proposed for a valuation method which evaluates the difference of how humans actually feel with their eyes. In this case, the color difference formula in the L*a*b* color system (CIELAB) which was most generally used was used, and the color difference was evaluated (JISZ8730). Table 1 shows classification of permissible color difference. In this valuation basis, permissible values of color of absolute quantity are defined as shown in Table 1. The difference that humans feel with their eyes is greater as the value of the color difference is greater. Accordingly, in the medical application, it can be safely said that discrimination of tissues becomes better as color difference is greater.

TABLE 1

| Extent of Color Diff | Denomination | Note |
|---|---|---|
| 0.3 | Discriminative Color Diff | Colorimetric reproduction accuracy of the same subject |
| 0.6 | Class 1 | Permissible difference limit in consideration of various factors in deviation |
| 1.2 | Class 2 | Substantially same when judging in side-by-side arrangement |

TABLE 1-continued

| Extent of Color Diff | Denomination | Note |
|---|---|---|
| 2.5 | Class 3 | Substantially same when judging in separate arrangement |
| 5 | Class 4 | Substantially same when comparing in different time point |
| 10 | Class 5 | Permissible value of marking pen |
| 20 | Class 6 | Color management of color name level etc. |

The respective emission spectrums of light sources used for acquiring color differences are shown in FIG. 1. In detail, the list of x values, y values in xy chromaticity diagram, $T_{cp}$, Ra, and R9 of light sources are shown in Table 2.

TABLE 2

| | x | y | $T_{cp}$ | Ra | R9 | Note |
|---|---|---|---|---|---|---|
| Standard Source C | 0.310 | 0.316 | 6775 | 98 | 85 | |
| Blackbody Radiation Light | 0.380 | 0.377 | 4000 | 100 | 100 | Light source close to the source used in an operation |
| Mass-Produced White LED | 0.300 | 0.298 | 7786 | 82 | 28 | |
| Two-Wavelength LED | 0.310 | 0.314 | 6798 | −44 | −272 | Combination of BG and R LEDs |
| Second Two-wavelength LED | 0.286 | 0.290 | 9353 | −81.7 | −606 | |
| 555 nm LED | 0.410 | 0.579 | — | — | — | |

Figure 2:
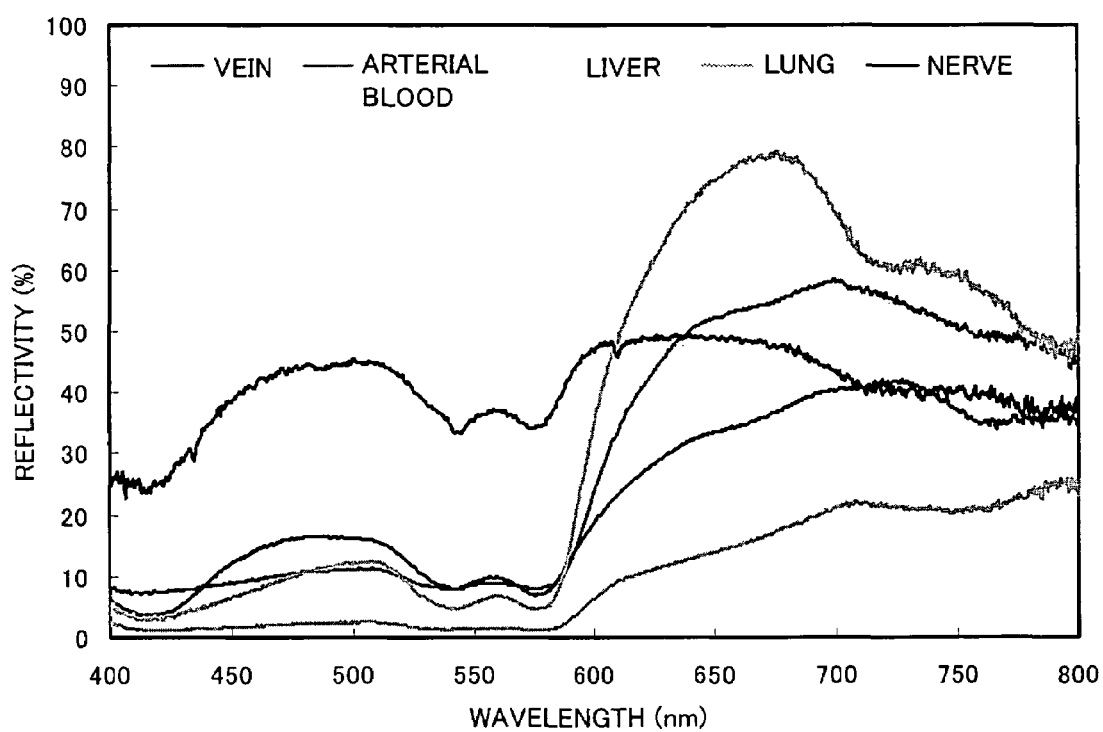
FIG. 2 is a graph showing reflectivity of reflection spectrum of each living body tissue used in one embodiment of the present invention.
Figure 3:
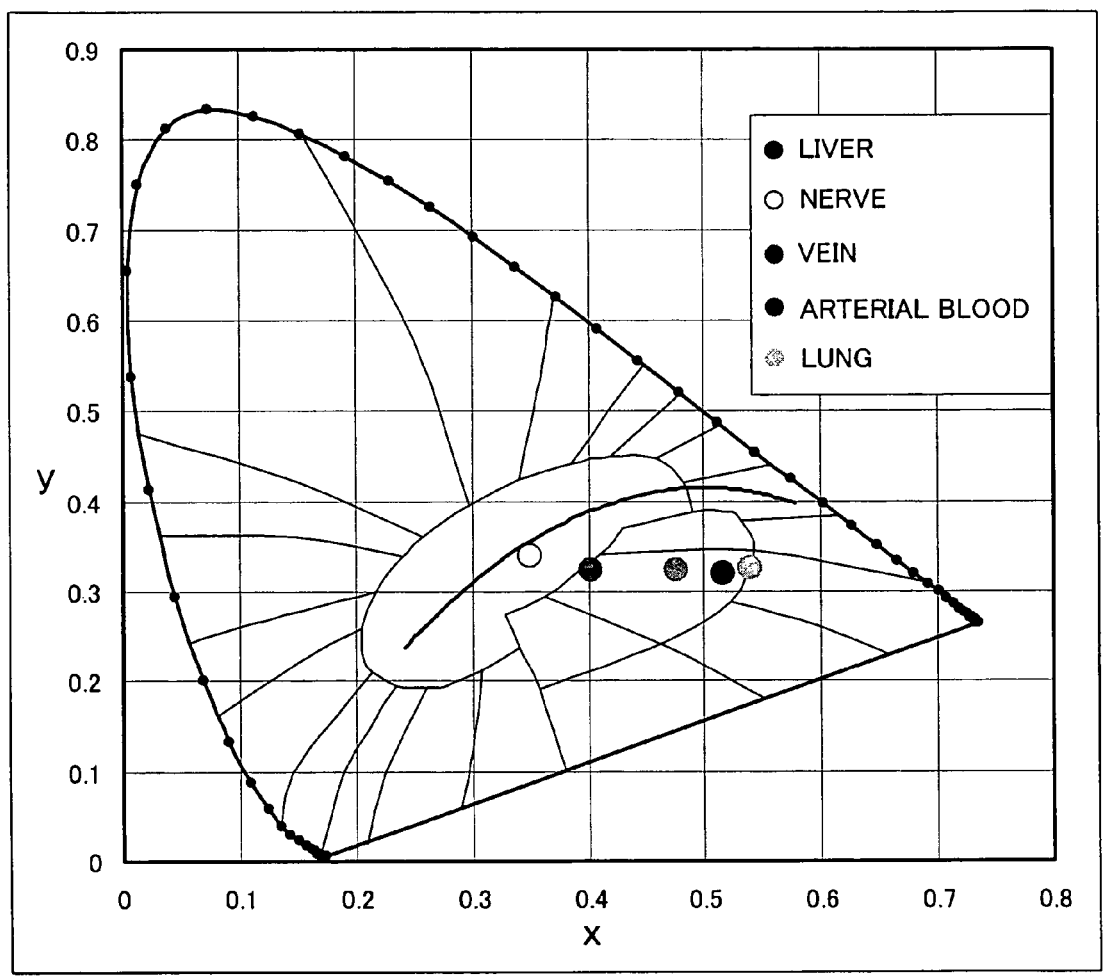
FIG. 3 is a graph showing a chromaticity coordinate of living body tissue of FIG. 2 on a CIE chromaticity diagram.

Various organs (a vein, an artery, liver, a lung, and a nerve, in this case) of a pig under anesthesia were irradiated with the above light sources in a living state. The spectrum of the reflected light was measured. The reflection spectrums in respective wavelengths are shown in FIG. 2. A plot graph of CIE chromaticity diagram is shown in FIG. 3. According to these results, it was found that the organs other than the nerve tissue could be identified by the reflection spectrum ratio between a bluish green range near 490 nm and a red range near 600 nm.

The following Tables 3 to 8 show calculated results of color differences between tissues when the various organs with these reflection spectrums were irradiated with the above various light sources. In these Tables, Table 3 shows the color differences of the reflection spectrums of the vein, arterial blood, liver and lung, in standard source C. Similarly, Tables 4 to 8 show the color differences of the reflection spectrums of them, in the blackbody radiation light, the mass-produced white LED, the two-wavelength LED, the two LEDs with wavelengths of 490 nm and 650 nm as the second two-wavelength LED, and the LED with wavelength of 555 nm, respectively. Table 9 shows tristimulus values (X, Y, Z), color coordinates (x, y), and CIE1976 (L*a*b*) color space as the color characteristics of the various internal organs. Table 10 shows the sums of the color differences of the above Table 3 to 8.

TABLE 3

| | Vein | Arterial Blood | Liver | Lung |
|---|---|---|---|---|
| Arterial Blood | 19.3 | | | |
| Liver | 25.2 | 25.3 | | |
| Lung | 37.4 | 18.2 | 36.8 | |
| Nerve | 29.9 | 41.0 | 54.5 | 54.9 |

TABLE 4

| | Vein | Arterial Blood | Liver | Lung |
|---|---|---|---|---|
| Arterial Blood | 21.2 | | | |
| Liver | 24.7 | 26.4 | | |
| Lung | 41.0 | 19.9 | 40.3 | |
| Nerve | 30.6 | 43.1 | 54.2 | 59.0 |

TABLE 5

| | Vein | Arterial Blood | Liver | Lung |
|---|---|---|---|---|
| Arterial Blood | 16.1 | | | |
| Liver | 25.1 | 24.3 | | |
| Lung | 31.9 | 16.2 | 33.2 | |
| Nerve | 29.8 | 36.0 | 53.1 | 47.8 |

TABLE 6

| | Vein | Arterial Blood | Liver | Lung |
|---|---|---|---|---|
| Arterial Blood | 34.8 | | | |
| Liver | 29.4 | 31.6 | | |
| Lung | 53.8 | 19.5 | 48.4 | |
| Nerve | 29.5 | 57.4 | 58.3 | 73.4 |

TABLE 7

| | Vein | Arterial Blood | Liver | Lung |
|---|---|---|---|---|
| Arterial Blood | 39.5 | | | |
| Liver | 29.5 | 35.1 | | |
| Lung | 60.7 | 21.6 | 54.4 | |
| Nerve | 36.4 | 71.4 | 64.1 | 90.2 |

TABLE 8

| | Vein | Arterial Blood | Liver | Lung |
|---|---|---|---|---|
| Arterial Blood | 9.6 | | | |
| Liver | 24.3 | 23.1 | | |
| Lung | 22.0 | 13.9 | 25.0 | |
| Nerve | 30.4 | 32.0 | 53.8 | 41.5 |

TABLE 9

| | X | Y | Z | x | y | L* | a* | b* |
|---|---|---|---|---|---|---|---|---|
| Light Source | 70.7 | 100.0 | 2.0 | 0.410 | 0.579 | — | — | — |
| Vein | 7.7 | 9.7 | 0.2 | 0.437 | 0.550 | 37.2 | 9.1 | −5.2 |
| Arterial Blood | 8.7 | 9.8 | 0.2 | 0.458 | 0.532 | 37.4 | 15.6 | 1.9 |
| Liver | 1.7 | 1.8 | 0.0 | 0.487 | 0.504 | 14.3 | 14.3 | 1.0 |
| Lung | 8.5 | 8.2 | 0.1 | 0.503 | 0.488 | 34.4 | 29.1 | 3.4 |
| Nerve | 26.9 | 36.7 | 0.8 | 0.418 | 0.571 | 67.1 | 4.1 | −1.9 |

TABLE 10

| Light Source | Color Temp. | Sum of Color Diffs. |
|---|---|---|
| Standard Source C | 6775 | 342.5 |
| Blackbody Radiation Light | 4000 | 360.4 |
| Mass-Produced White LED | 7786 | 313.5 |
| Two-Wavelength LED | 6798 | 436.1 |
| Second Two-Wavelength LED | 9353 | 502.9 |
| 555 nm LED | — | 275.6 |

As is evident from Table 10, in the two-wavelength LED, the amount of color difference was improved 20% or more as compared with the blackbody radiation light. Accordingly, it is possible to provide an image with more sufficient contrast. Furthermore in the second two-wavelength LED, the amount of color difference was improved about 40%. Therefore, when the two-wavelength LED is used, it is possible to provide color difference similar to or superior to a conventional shadowless lamp. For this reason, the two-wavelength LED can be preferably used as a light source for a medical lighting apparatus.

According to the above result, it was found that the reflectivities of the tissues other than the nerve reduced in the wavelength range of about 525 nm to about 590 nm, as seen from FIG. 2. Although the reason is not clear, the reason is assumed that hemoglobin or oxyhemoglobin in blood absorbed light. Since the wavelength range of 525 to 590 nm does not contribute to identification of tissues, the reflection spectrum, which provides easy identification of tissues, can be obtained by reducing the reflection spectrum of this range. According to the experiment conducted by the inventors, a light source, which provides easy identification of living body tissues, could be obtained by setting the ratio which of the range of wavelength 525 to 590 nm to the spectrum of the range of wavelength 380 to 780 nm corresponding to visible light components is not greater than $\frac{1}{5}$, preferably $\frac{1}{10}$. This can be also confirmed from the chromaticity diagram shown in FIG. 3. The reflection spectrums of various organs substantially align on the line which connects between dominant wavelengths $\lambda_d$ of 495 nm and 615 nm. Accordingly, a light source suitable for identification of living body tissues can be obtained by mixing two colors of blue or bluish green light corresponding to a wavelength of about 495 nm, and red light corresponding to a wavelength of about 615 nm. According to the detailed experiment conducted by the inventors, when the bluish green light component with peak wavelength of 430 to 520 nm, preferably 480 to 510 nm was used, a light source with more excellent characteristics could be obtained. In addition, when the red light component with a peak wavelength of not less than 600 nm, preferably 610 to 670 nm was used, a light source with excellent characteristics could be obtained. Therefore, lighting optimized for medical applications can be obtained by a combination of these two colors. The combination of the two colors is adjusted so that they have a complementary color relationship, in other words, so that color mixture provides white light. The reason is that white light is the most natural as lighting, and gives a peace of mind for medical workers. Thus, white light is preferable. It is generally considered that a color mixture of the RGB that are three primary colors of light is outstanding as a white light source. However, in medical applications, a light source suitable for sharply identifying living body tissues can be obtained by a color mixture of the two colors, blue or the bluish green color and red color, as mentioned above.

As mentioned above, color temperature in the living body tissues other than the nerve is high, thus, they can be identified based on color difference by reducing component with wavelength 525 to 590 nm. On the other hand, it was not observed that the nerve tissue remarkably absorbed light in the above wavelength range as shown in FIG. 2 dissimilarly to other tissues. In the Y values (representing brightness) of Table 9, the nerve is 36.7 while other organs are 10 or less. From this point of view, it is advantageous to identify the nerve tissue by brightness difference rather than color difference. In this method, color reproduction is not necessary; it is possible to distinguish the nerve tissue from other tissues only by brightness difference in monochromatic radiation, that is, contrast. In this case, it is preferable that the green light component which can provide a clear difference between the nerve tissue and other tissues is used, according to FIG. 2. Specifically, according to experiment conducted by the inventors, a light source with a peak wavelength in the range 520 to 590 nm is used. Its spectral half-value width is not greater than 70 nm, preferably not greater than 60 nm, and more preferably not greater than 50 nm. Subjects are sharply irradiated only with the green component by narrowing its spectral half-value width, in other words, broadcloth spectrum is eliminated to reduce other spectrum components, and thus, it is possible to easily identify the nerve tissue from other tissues. For this reason, a light source which can adjust only the green light component is used. For example, a green LED with the above spectrum is used, and configured so that its light output can be independently adjusted. Only a green LED is used and radiates subjects, thus, it is possible to identify the nerve tissue by brightness difference under yellowish green lighting.

This construction is preferably combined with the aforementioned construction suitable for living body tissues other than the nerve. That is, a light source of the combined construction has three colors of LEDs, an LED with peak wavelength 430 to 520 nm as bluish green light component, an LED with a peak wavelength not less than 600 nm as the red light component, and an LED with a peak wavelength of 520 to 590 nm as the green light component. In the case of identification of tissues other than a nerve tissue with this light source, the green LED is turned OFF or set to reduce its output, and the red and blue LEDs are adjusted to identify organs by the color difference between them. On the other hand, in the case of identification of a nerve tissue, the red and blue LEDs are turned OFF or set to reduce their output, and only the green LED is adjusted to identify the nerve tissue by the contrast. Accordingly, it is possible to provide medical lighting apparatus that is optimized for identification by varying the setting of the light source according to purpose or situation.

Figure 4:
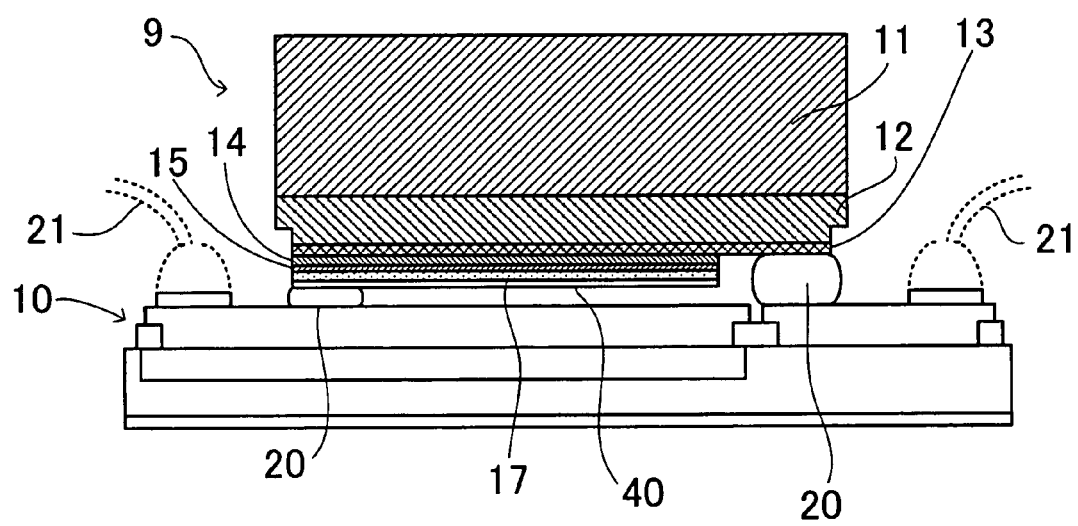
FIG. 4 is a cross-sectional view of a light emitting element of a lighting apparatus according to one embodiment of the present invention.

In the above embodiment, LEDs (light emitting diodes) were used as the light source. One example of an LED is shown in FIG. 4. In this figure, an LED chip 9 of nitride semiconductor light emitting element is mounted on a submount 10 which is one of a wiring board by flip chip mounting. Dissimilarly to face-up mounting in which the electrode formation surface of nitride semiconductor layers serves as a chief ray outgoing surface, flip chip is a mounting method in which the substrate side opposed to an electrode formation surface serves as a chief ray outgoing surface. It is also referred to as face-down mounting, and so on. In the LED chip 9 of FIG. 4, a buffer layer 12, an n-type nitride semiconductor layer 13, an active layer 14 and a p-type nitride semiconductor layer 15 are epitaxially grown on the substrate 11 in this order, and a transparent conductive layer 17 and a metal-electrode layer 40 are laminated thereon. Methods, such as a metal-organic chemical vapor deposition (MOCVD) method, hydride vapor-phase-epitaxyl method (HVPE), hydride CVD method, and MBE (molecularbeam epitaxy), can be used as the crystal growth method. Homo structure, hetero structure, double-hetero structure, and so on with MIS junction, PIN junction or PN junction can be used as the laminated structure of the semiconductor layer. A superlattice structure can be applied to any layer. The active layer 14 can have a single or multiquantum quantum well structure provided with thin layer(s) for quantum effect. In FIG. 4, a reflective layer provided on the transparent conductive layer 17 is omitted for ease of illustration. Though not illustrated in detail, a part of the active layer 14 and the p-type nitride semiconductor layer 15 is selectively removed by etching to partially expose the n-type nitride semiconductor layer 15, thus, an n-side pad electrode is formed in FIG. 4. A p-side pad electrode is formed on the p-type nitride semiconductor layer 15 in the same surface side of the n-side electrode. Metallizing layers (bumps 20) for connection with external terminals or the like are formed on the pad electrodes. The metallizing layer is made of a material, such as Ag, Au, Sn, In, Bi, Cu, or Zn. The electrode formation surface side of LED chip 9 is opposed to one pair of positive and negative external terminals provided on the submount 10. The electrodes are jointed with bumps 20. Wires 21 and so on are wired onto the submount 10. The principal plane side of the substrate 11 of the LED chip 9 mounted in face-down mounting serves as the chief ray outgoing surface. The nitride semiconductors are formed of general formula $In_xAl_yGa_{1-x-y}N$ ($0 \leq x$, $0 \leq y$, $x+y \leq 1$), and can be mixed with B, P, or As. The n-type nitride semiconductor layer 13 and the p-type nitride semiconductor layer 15 are not specifically limited to a single layer or multiplayer structure. The nitride semiconductor layers can contain an n-type or p-type impurity if necessary. The n-type impurity can be a IV or VI group element, such as Si, Ge, Sn, S, O, Ti or Zr, preferably Si, Ge or Sn, and more preferably Si. The p-type impurity can be Be, Zn, Mn, Cr, Mg, Ca or the like, and preferably Mg, but is not specifically limited to these. Thus, the nitride semiconductors of each conductivity type can be formed. In the aforementioned nitride semiconductor layer, the active layer 14 is included. This active layer 14 has a single (SQW) or multiquantum well structure (MQW).

The above LED can adjust peak wavelength by adjusting the composition ratio and the dopants and can be used preferably in the present invention. Particularly, since an LED has an excellent monochromatic peak wavelength, it is advantageous for adjustment of the reflection spectrum. Combining a wavelength conversion member, such as a phosphor, with the LED can provide adjustment to a desired wavelength. A phosphor is dispersed in the mold resin which molds LED. The phosphor absorbs a part of light emitted from the LED, converts the wavelength, and emits different light. Thus, a desired light is emitted by color mixture of light of LED and light with wavelength converted by the phosphor. This type of wavelength conversion member is formed of bound phosphor particles. After binder containing phosphor particles is applied to the surface of a package on which LED is arranged, organic solvent of the binder is vaporized. Thus, the phosphor is formed on the surface of the package on which the light emitting element is arranged.

In this embodiment, light emitting devices other than LED can also be used. Although various light sources can be used as a lighting apparatus of the present invention, a nitride semiconductor device, which is formed of laminated semiconductor layers by using nitride semiconductor of $In_xAl_yGa_{1-x-y}N$ ($0 \leq x$, $0 \leq y$, $x+y \leq 1$), for example, has excellent characteristics, such as low power consumption and long life, and thus can be preferably used. Not only LED but also LD (laser diode), EL, and so on can be used as a semiconductor light emitting device. Particularly, LD is preferably used due to its excellent color discrimination characteristics. An existing lamp can also be used. High brightness lamps, such as halogen lamp, xenon lamp, and metal halide lamp, can be used as a light emitting body. In order to adjust the wavelength of the light emitted from these light emitting bodies to the above conditions, a wavelength conversion member can be combined. A phosphor, a filter, or the like, which absorbs light emitted from the light emitting body and converts it into light with different wavelength, can be used as the wavelength conversion member.

Colored glass, special glass, a glass case filled with pigment solution, or the like can be used as the filter. A light source which has the above characteristics as a medical light source can be used as room light in an operating room, small light, light for an endoscope, a goggles lamp attached to goggles, and so on. Not only a light source but also a filter and an image display can be used in the above applications. That is, even if a conventional light source or a conventional image display are used, adding the filter in a hardware or software manner can cut or reduce the component in the aforementioned wavelength range. Accordingly, it is possible to obtain spectrum which provides easier identification of living body tissues. For example, when the band pass filter which cuts the aforementioned wavelength range is mounted in a software manner as image processing, it is possible to display an image which provides easier identification. Therefore, characteristics, which are ideal in a medical application, can be obtained. Similarly, in goggles which a medical worker wears, when a filter which cuts the aforementioned wavelength range is attached onto a field surface, or transparent glass itself has such function, living body tissues can be easily identified through the goggles. In addition, since a luminosity factor is generally reduced when a filter is used, adjustment such as an increase of the amount of light is preferably performed to improve the luminosity factor. In this specification, a filter apparatus refers to an apparatus including protective gear such as glasses for protection of a worker's eyes. An image display refers to an apparatus, which forms and displays an image by using optical photoreceptor elements, such as a CCD camera and an endoscope. In this display, in addition to hardware-based methods for adjustment of color difference, such as adjustment of sensitivities of photoreceptor elements, and allowing light to pass through the filter of optical system, the present invention can be applied to a software-based method for processing of the spectrum components of RGB of image acquired by means of an existing hardware. These methods are included in the scope of the present invention.

Figure 5:
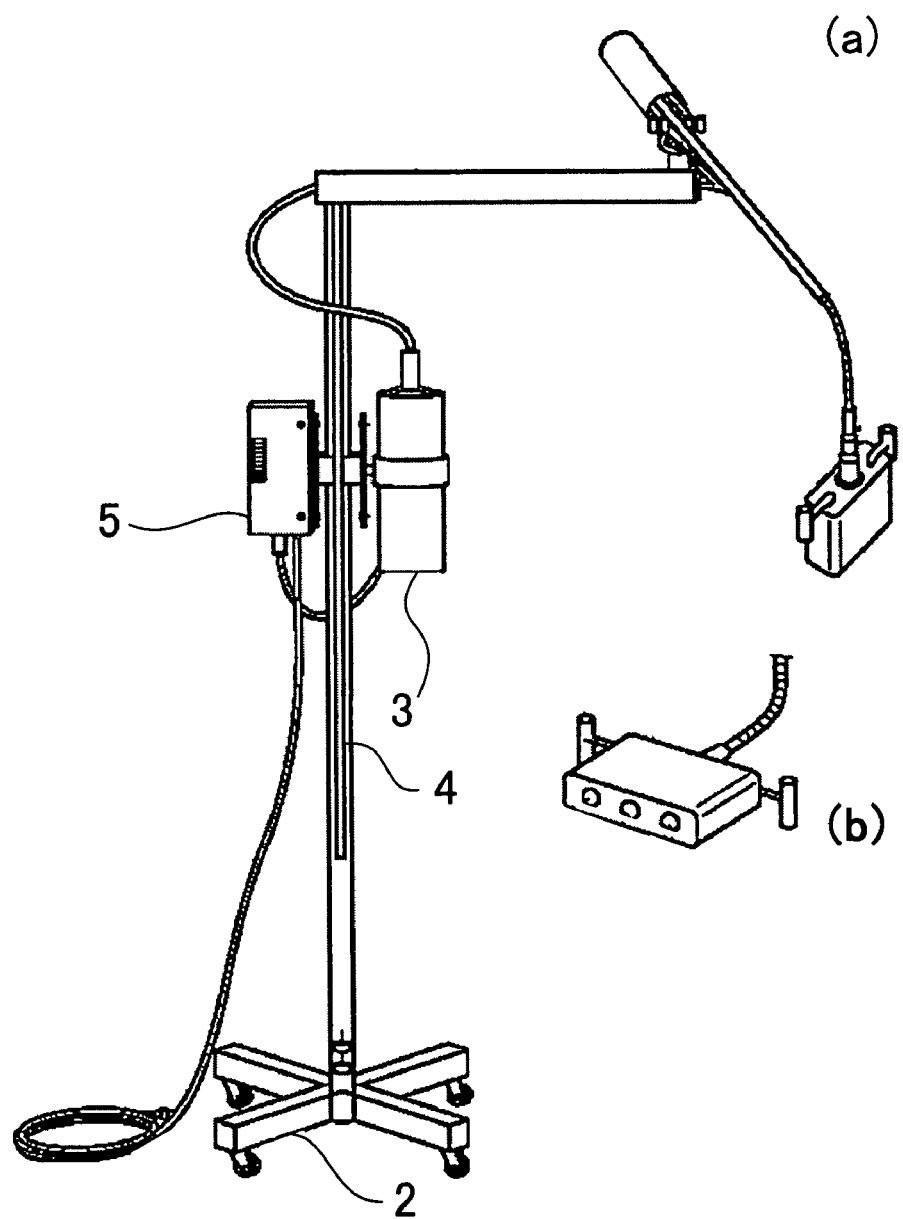
FIG. 5 is a perspective view showing a medical lighting apparatus according to one embodiment of the present invention.

FIG. 5 shows medical lighting as one example of an exemplary lighting apparatus. FIG. 5(*a*) shows a perspective view of the whole medical lighting. FIG. 5(*b*) shows a perspective view of a light head portion. As shown in FIG. 5, in the medical lighting, a light source unit 3 and a power supply unit 5 are provided on a pole 4 which stands straight on a movable mount 2 so that their positions are adjustable in the vertical direction. A light source which has the aforementioned characteristics is used as a light source included in the light source unit 3. Light beams are led to the necessary position through an optical fiber, and their exposure fields irradiated from a light output portion are overlaid. Accordingly, irradiation which achieves the shadowless effect is performed, and identification of living body tissues can be improved.

Figure 6:
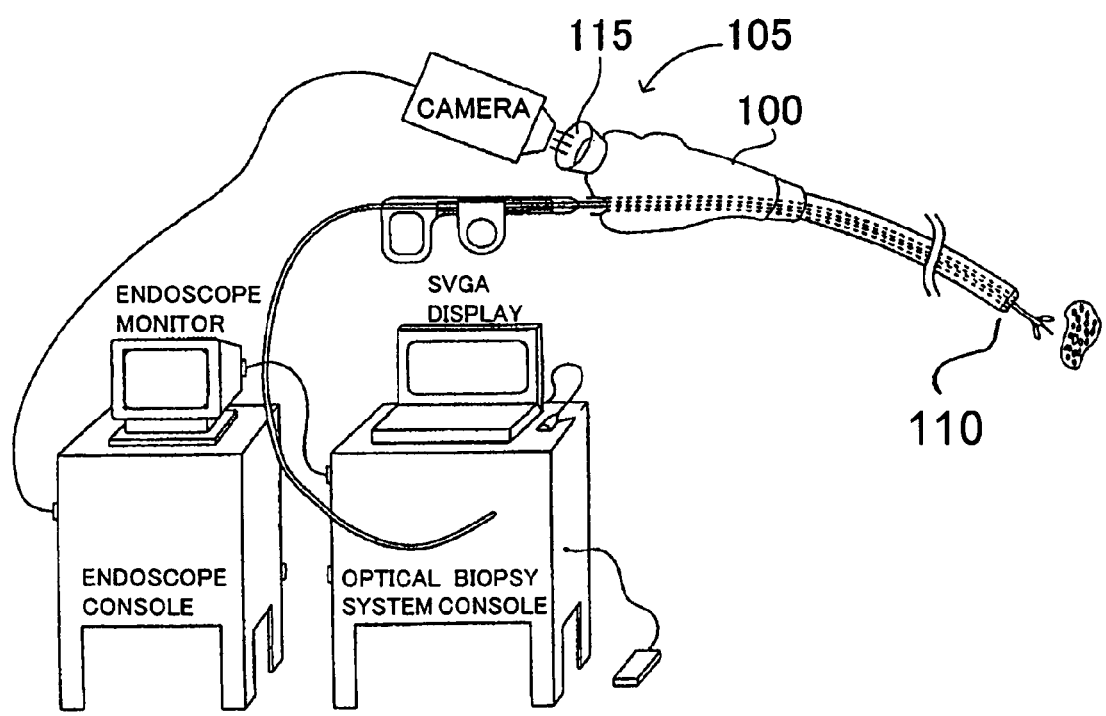
FIG. 6 is a perspective view showing a medical image display according to one embodiment of the present invention.

FIG. 6 shows an endoscope system as one example of medical image display. This figure is a perspective view of the endoscope system for tissue diagnosis. The system has an endoscope 100 for examining the interior of patient's respiratory tract, upper or lower gastrointestinal tract, urinary tract, or the like. An observation optical system 115 includes an optical fiber extending internally of the endoscope 100 for providing illumination at a distant end 110. The observation optical system 115 includes an optical fiber extending internally of a close end 105 of the endoscope 100 for observing the image at the distant end 110. In this system, the aforementioned light source can be used as an excitation light source. Alternatively, in a system which forms an image by means of a photoreceptor element, such as CCD, a desired reflection spectrum can be obtained by adjusting the photosensitivity of the photoreceptor element. For example, photosensitivity of each color in CCD, which receives RGB light components, is varied, or turned ON/OFF for each of RGB to increase/decrease the green component of reflection spectrum, and thus, the visibility of organs is improved.

In addition, the electric processing may adjust the spectrum component without changing the construction of the light source or photoreceptor element so as to improve identification of living body tissues in the image which is finally displayed. For example, a band-pass-filter circuit, which passes or removes only the aforementioned wavelength band, is added. Alternatively, signals are processed by using a filter function, which achieves such filtering function, and the image is processed.

Figure 7:
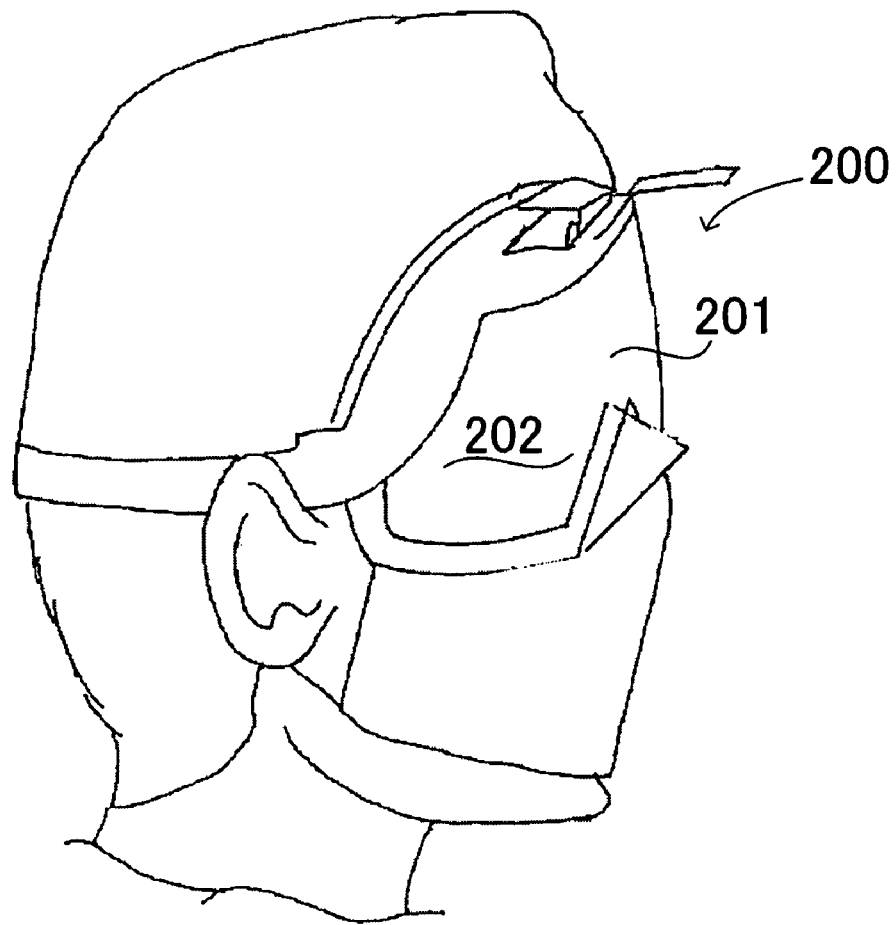
FIG. 7 is a perspective view showing a medical filter apparatus according to one embodiment of the present invention.

FIG. 7 shows medical protection goggles as one example of a medical filter apparatus. A filter 201 is attached onto the field surface 201 of the goggles 200. Needless to say, in the case of light attached to the goggles, or goggles with light, the aforementioned light source can be used as light for these types of goggles.

Figure 8:
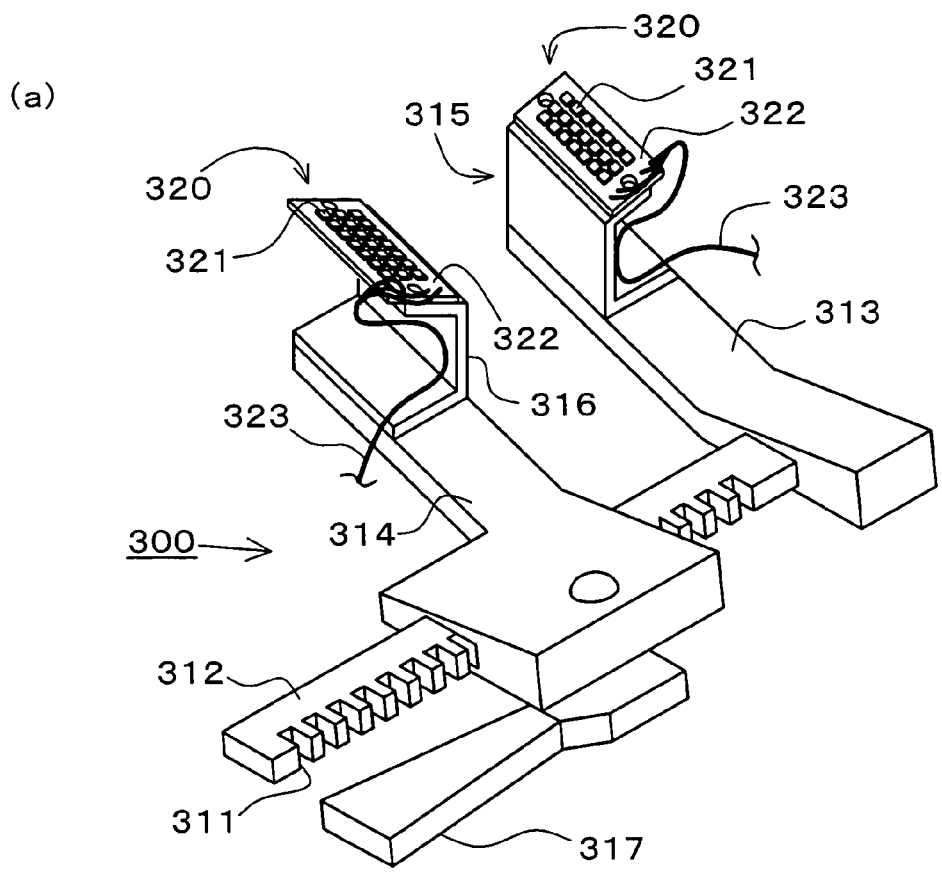
FIG. 8 is a perspective view showing a lighting apparatus according to another embodiment of the present invention.
Figure 8:
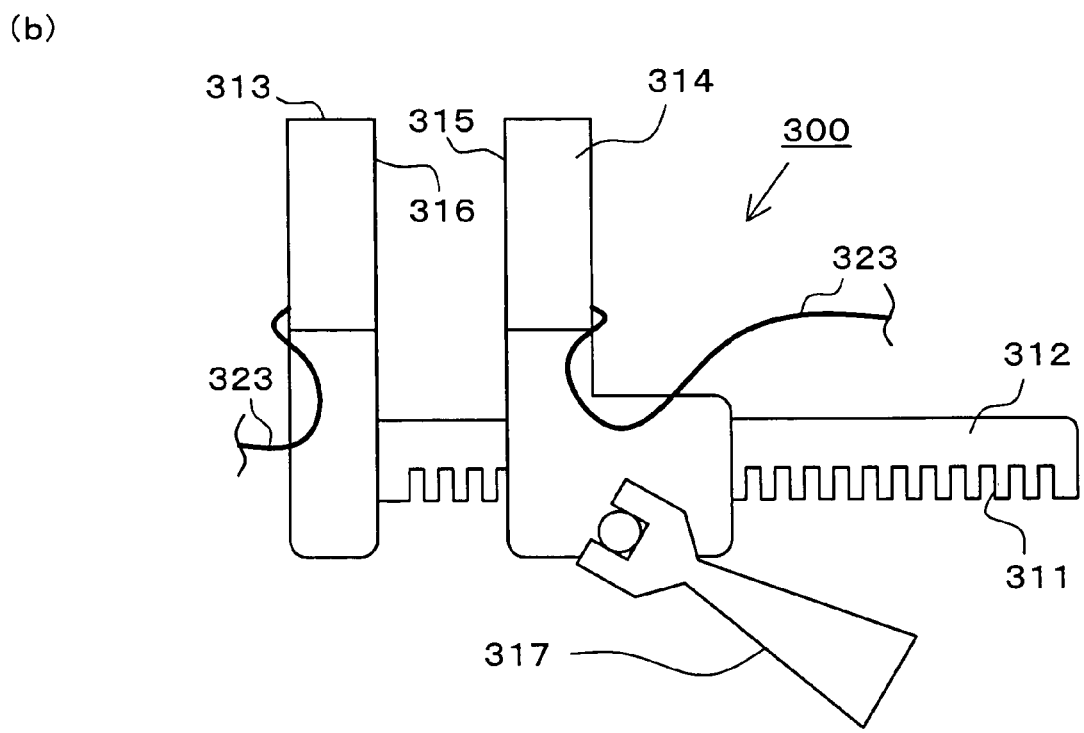

The present invention can also be used for a retractor shown in FIG. 8 as another example of lighting apparatus. FIG. 8(a) is a perspective bottom view of the retractor 300. FIG. 8(b) is a plan view of the retractor 300. The retractor is used to open and hold an incision during a surgical operation. Various types of retractors are used depending on operation parts and purpose. FIG. 8 shows the retractor 300 for chest surgery as one example of the retractor. This retractor for chest surgery has a base bar 312 with gear teeth 311 cut on its one side, first and second arm portions 313 and 314 perpendicular to the base bar 312. The first arm portion 313 is secured to the base bar 312. The base of the second arm portion 314 is inserted on the base portion of the base bar 312 and slidably attached along the base bar 312. Blades 315 and 316 are provided perpendicular to the respective arm portions at the respective ends of the arm portions opposite to the base bar 312. A handle 317 and gear (not shown) are provided in the base of the second arm portion 314, and this gear meshes with the gear teeth 311 cut on the base bar 312. When the handle 317 is rotated, the gear rotates, thus, the second arm portion 314 slides along the base bar 312. In operation, after the aforementioned pair of blades 315 and 316 is inserted in an incision part of the chest in the closed state, the space between the blades 315 and 316 is increased while they are kept in substantially horizontal posture by rotating the handle 317, thereby pushing and opening the ribs. Since the space of the blades 315 and 316 can be held at a certain distance, operations can be conducted while the incision part is opened wide.

Figure 9:
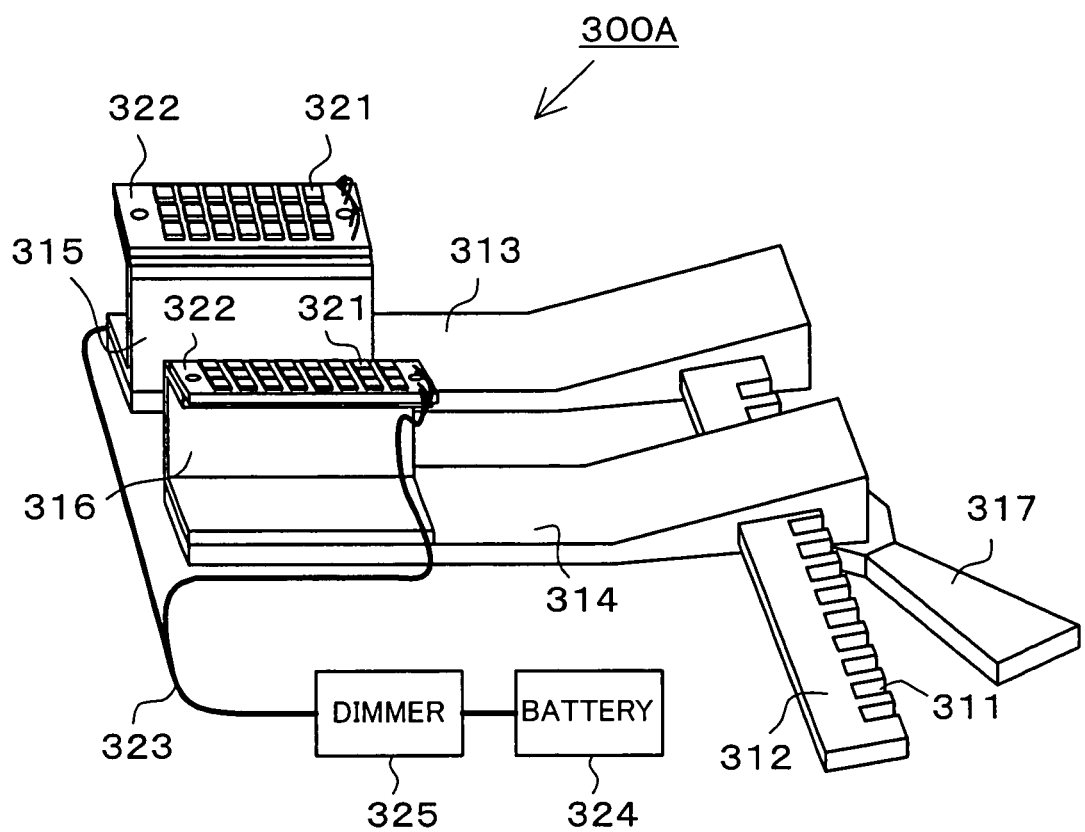
FIG. 9 is a perspective view showing a retractor which is previously developed by the inventors.

Generally, in the case of the surgical operation, in order to minimize patient's external injury and to accelerate postoperative recovery, it is desirable to make the opening as small as possible. However, when the retracted part is narrow, it is difficult to observe the deep interior, and ceiling lighting and so on cannot sufficiently illuminate the operation area in the body cavity. For this reason, while an endoscope or the like is inserted internally of the body, the image is obtained from the side of the retracted part, and the interior is observed, while operations are conducted. However, when the interior is illuminated by an optical fiber provided at the fore end of the endoscope, there is a problem that is hard to observe the interior caused by a shadow of surgical knife. In order to solve such a disadvantage, as shown in FIG. 9, the inventors have previously developed a retractor, which can prevent an appearance of shadow with illumination from both sides by adding LED lighting means at the fore end portions of blades of the retractor (Japanese Patent Application TOKUGAN 2003-291975). In a retractor 300A shown in FIG. 9, an LED is connected to a battery 324 and with a dimmer 325 by a cord 323.

In this type of retractor, the aforementioned lighting apparatus described in the embodiment is additionally used as the lighting means, thus, it is possible to provide medical lighting which provides easy color distinction and excellent visibility. An LED lighting apparatus 320 is arranged at the fore end portion of the blade to be inserted in an incision part, in the retractor 300 shown in FIG. 8. LEDs are arranged provided at the fore end of the retractor 300, and thus, the operation area in the body cavity can be illuminated. In addition, it is not necessary to separately provide a light source portion. Accordingly, it is possible to provide a simple and small construction, and to improve workability during an operation. In the case where an LED module 321 with a high thermal conductive base is used, it is possible to provide a large amount of and wide range illumination. In addition, heat generated by LED is efficiently diffused to the main body of retractor 300.

Particularly, in a retractor, since insertion of the blade into a body cavity is difficult, the lighting apparatus attached to the retractor is required to be thin to avoid disturbance of the operation. From this viewpoint, the aforementioned lighting apparatus can be easily thinned by using the LED, therefore, it is ideal as a lighting apparatus attached to a retractor. When an operation on the heart is conducted with a retractor, for example, since blood vessels and nerves closely exist in a heart, it is desired to sharply identify them to avoid accidental damage. Especially, in an operation on a child's heart, it is required to accurately conduct the operation so that they should not need pacemakers in the future. In such an operation field in which it is required to sharply identify between an organ and a nerve, a lighting apparatus capable of providing sharp color distinction is attached to a retractor, and thus, it is possible to provide a very suitable lighting environment. Therefore, it is very useful.

Although the fore ends of blades are bent at a right angle in a conventional retractor, when the present invention is applied to a retractor for a chest surgical operation, and so on, it is preferable that the bend angle is small, and the fore ends are inclined toward the insides of both blades (cants are provided), in this embodiment. Since irradiation light from the LED has high directivity, in the state where the fore end is right-angled, when the space between the arm portions is set too large, light may not be incident on the center. On the other hand, cants are provided at the fore end portions, and thus, the irradiation light can be collected in the center.

In the example of FIG. 8, the lighting apparatuses 320 are arranged on a pair of blades, respectively. The lighting apparatus may be attached only on the blade in one side, or the three or more lighting apparatuses may be attached on the blades.

It is preferable that the LED module 321 with LED chips integrated on a circuit board is used as the LED provided at the fore end of the blade. Accordingly, as compared with the case where the LED unit with LED chips covered packages by transparent resin or glass is used, many LED chips can be arranged in the small space, thus, it is possible to provide a large amount of light. When the size of LED module 321 and the number of LED chips arranged on the circuit board are changed, the LED module 321 with various amounts of luminescence intensity can be produced. Accordingly, the LED module 321, which is suitable for the purpose, can be used. The LED module 321 with the suitable size or with suitable numbers of LED chips can be used depending on the area or shape of the attachment part. It is preferable that solder terminal portions of the LED module 321 are coated with silicon resin. This can eliminate detachment of a small solder ball from a LED reflow junction portion and may fall into the inside of the patient's body. Since it is used for medical applications, from the viewpoint of safety, it is preferable to use Pb-free solder.

Although an LED has a feature that has high energy conversion efficiency and a reduced amount of heat generation, when many chips are integrated, the amount of heat generation becomes naturally large. In this embodiment, since the LED module 321 is attached to the fore end of the retractor 300 and is used inside the patient's body, the heat generation is not a negligible problem. In this embodiment, a high thermal conductive base is used in the LED module 321, the substrate is attached so as to be in intimate contact with the retractor 300. The heat produced in the LED chips is efficiently diffused through the base to the main body of the retractor 300. As such a high thermal conductive base, for example, a diamond substrate proposed by the applicant of the present invention in Japanese Laid-Open Publication Kokai No. 2002-329896, an alumina substrate, an aluminum nitride ceramic substrate, an aluminum substrate, or the like can be used. The body of the retractor 300 is formed from materials with the high thermal conductivity, such as aluminum, and thus, its heat capacity increases. Accordingly, it is possible to sufficiently absorb and diffuse heat produced from the LED chips. As mentioned above, the retractor 300 itself serves as a heat diffusion member, and thus, the heat is radiated efficiently. It is possible to prevent influence on a part to be operated on such as low-temperature burn due to heat generation of the lighting apparatus 320. The LED module 321 may be attached to an excellent thermal conductive plate 322, and the plate 322 may be attached to the retractor. In this case, even when a plurality of LED modules is attached, the modules can be easily attached.

In order to prevent burn caused by direct contact of a high temperature part of the LED or plate 322 with the tissue inside the patient's body during the operation, it is preferable to cover the whole LED attachment portion with a capsule of transparent glass or heat-resistant plastic, and so on. This construction improves the heat diffusion characteristics as mentioned above. Contrary to the aforementioned construction to improve heat diffusion, this construction to cover the whole LED attachment portion can be also used in the case where the heat generated from the LED chips is confined in the LED chips. Particularly, in the case where the whole LED attachment portion is used as a disposable type to prevent infections in medical applications, since it is not necessary to consider the deterioration and life of the element, the whole LED attachment portion can have heat insulation structure so as to prevent leakage of the heat generated in the LEDs. For this purpose, it is preferable that a base with excellent thermal insulation is used, for example, glass epoxy group base or the like can be used. In this case, since a multilayer base can be used, the flexibility of arrangement of LED chips increases as compared with the case where an aluminum base is used. For example, the RGB of LED chips can be alternately arranged so as to be dispersed. In this case, it is possible to improve the color mixture characteristics. An LED package, which has RGB of LED chips integrated in one package and can exhibit multicolor emission, may be used. In this construction, since the RGB chips are arranged to be adjacent to each other in the same package, the color mixture characteristics are excellent. For example, it is possible to prevent deterioration of color mixture characteristics due to a shadow cast by only one chip in the case where RGB LED chips are spaced away from each other. Therefore, it is possible to provide high quality illumination with excellent color-reproduction characteristics.

Figure 10:
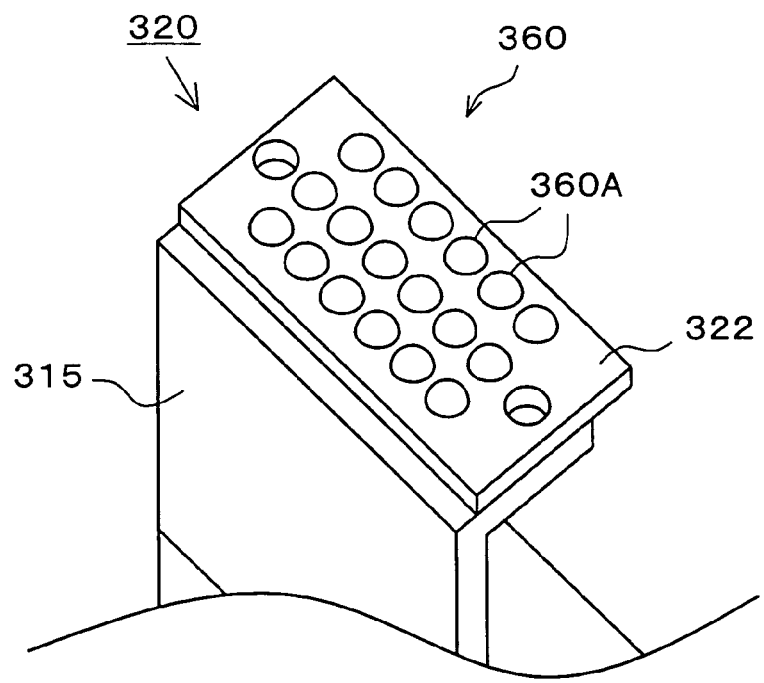
FIG. 10 is a perspective view showing one example of lighting apparatus in which a lens is formed on the surface of LED chip.
Figure 11:
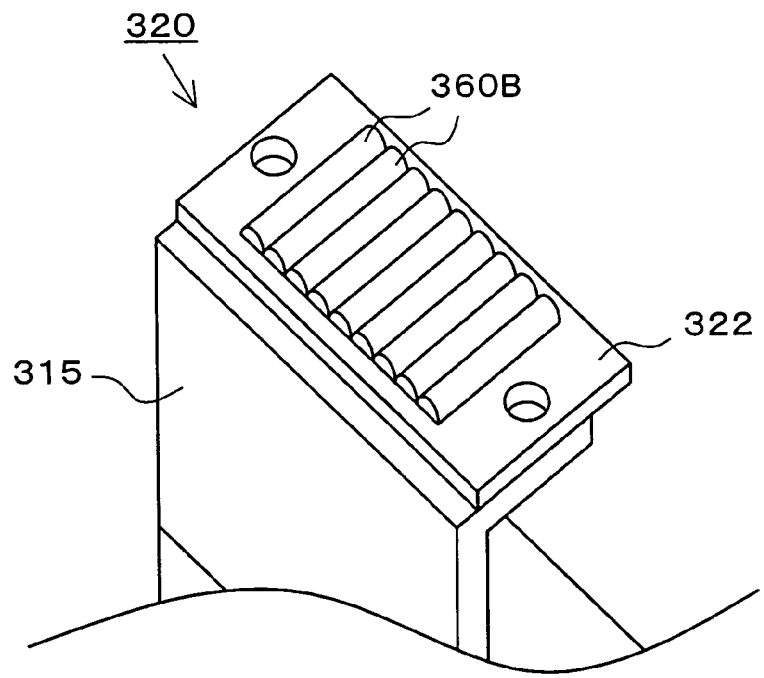
FIG. 11 is a perspective view showing another example of lighting apparatus in which a lens is formed on the surface of LED chip.
Figure 12:
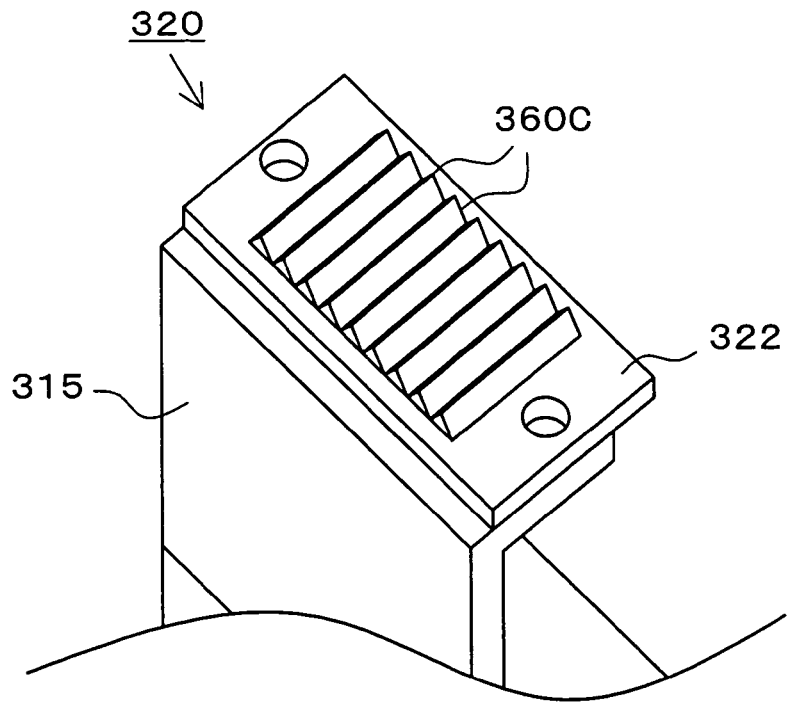
FIG. 12 is a perspective view showing still another example of lighting apparatus in which a lens is formed on the surface of LED chip.
Figure 13:
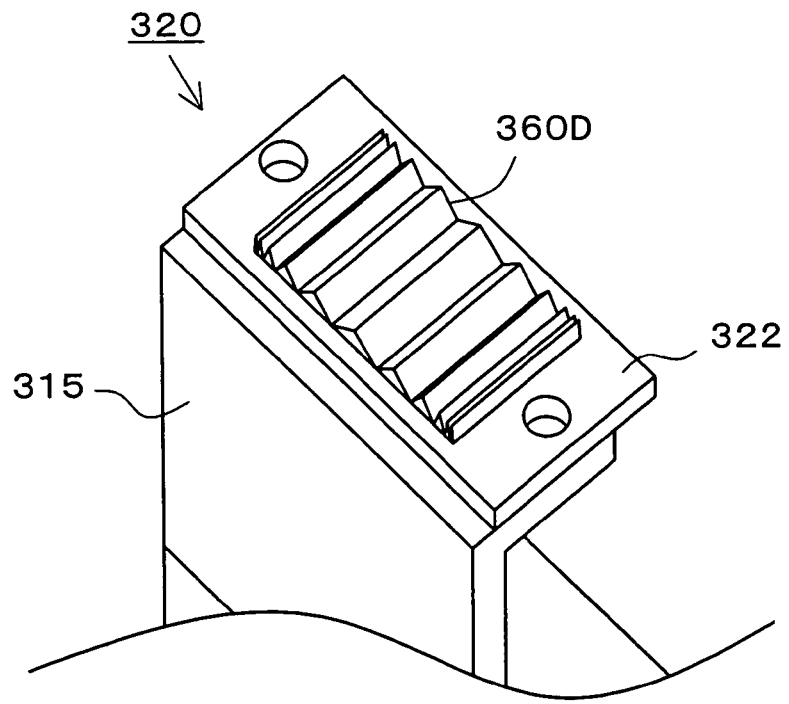
FIG. 13 is a perspective view showing still another example of lighting apparatus in which a lens is formed on the surface of LED chip.

A lens 360 is formed on the surface of the LED chips arranged in the lighting apparatus 320 preferably as shown in FIGS. 10 to 13. Accordingly, light emitted from the LED chips is collected, and the brightness can be improved. This can contribute low power consumption, and reduction of the amount of heat generation by reducing the number of LED chips used therein. The lens 360 is formed in individual dome shapes 360A corresponding to every LED chip as shown in FIG. 10. Alternatively, it can be formed in cylindrical lens shapes 360B aligned with a plurality of LED chips as shown in FIG. 11, or in triangular prism shapes 360C as shown in FIG. 12. Shapes in the lens 360 may not be the same for every LED chip, but the patterns may be changed depending on their positions. For example, as shown in FIG. 13, in order to collect the light from LEDs, the lens may be formed so that the inclination of triangular prism-shaped lens 360D in the center of the LED module is obtuse, and the inclination becomes acuter as the end of LED module approaches. In this example, although the inclinations of the lens extends only in the longitudinal direction of the LED module, the inclinations may vary in the width direction of the LED module. The patterns are also individually formed in dot shapes and so on for every LED chip.

Figure 14:
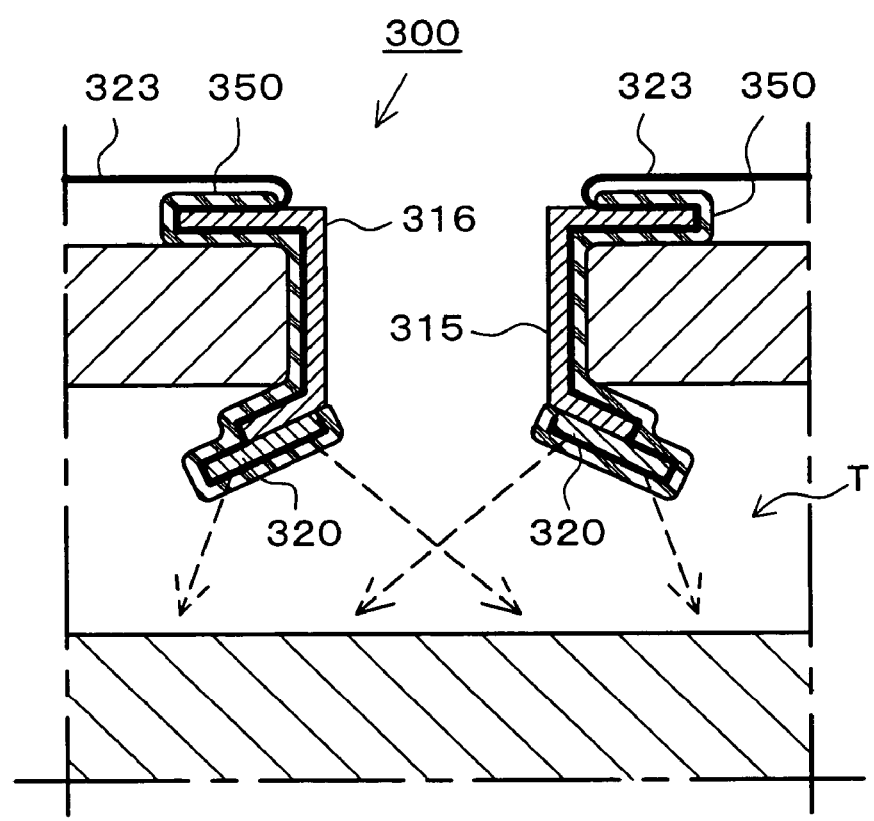
FIG. 14 is a cross-sectional view showing an example of use of the retractor of FIG. 8.

FIG. 14 is a cross-sectional view showing the state where the inside of body cavity T is illuminated by using the retractor 300. As shown in this figure, in the state where the patient's part to be operated on is incised, the retractor 300 is inserted, and the pair of blades 315 and 316 each outside of which opens in a U-shape is moved by handling the handle 317 so that the interval between them increases, thus, the part to be operated on is opened. In this state, the lighting apparatuses 320 fastened at the fore ends of the blades 315 and 316 illuminate the inside of the body. As mentioned above, this lighting apparatus 320 can be adjusted and changed to conditions suitable for observation depending on each type of cells such as nerve and organs. Accordingly, it is possible to provide lighting that is optimized for the operations.

The plates 322 are fastened to the blades 315 and 316. Alternatively, they can be detachably attached for ease of maintenance or replacement. Particularly, it is difficult to use hot alcohol on the electronic components, which compose the lighting apparatus 320, such as LED chips, to kill bacteria. It is preferable that the electronic equipment is detachable as single-use equipment for a single operation for medical applications.

As shown in the cross-sectional view of FIG. 14, in the attachment of the lighting apparatus 320 to the retractor 300, in the state where the lighting apparatuses 320 are set to the blades 315 and 316, the covers 350 cover the surfaces of the blades 315 and 316, for example. This can secure them without using small members, such as screws. Accordingly, it is possible to prevent foreign matter, such as screws, from falling and remaining in the inside of the body. The cover 350 is integrally formed of resin with excellent resistance to bactericidal treatment and so on, such as silicone resin, for example. It is preferable that positioning members, such as pins and holes are provided in the plates 322 and the attachment parts of the blades 315 and 316. The cover 350 is configured to cover the U-shaped opening portion side as shown in FIG. 14. Accordingly, it is possible to ensure that the opening part of the retractor 300 can be made wide. Since the cover 350 is disposable, it is possible to prevent infection and so on, and to improve safety. As mentioned above, the cover 350 can achieve fixation and surface protection of the lighting apparatus. However, a construction, which directly attaches the lighting apparatus to the blade by using an engaging member, such as a hook, without using the cover, may be used.

In addition, in the case where the cover and the lighting apparatus are disposable, a certain method for preventing accidental reuse may be added. For example, grain processing is performed on the whole or a part of the surface cover which covers the LED chips. Thus, stains, such as blood, tend to adhere to the surface. Since stains tend to adhere to the surface, it is possible to prevent accidental reuse.

Figure 15:
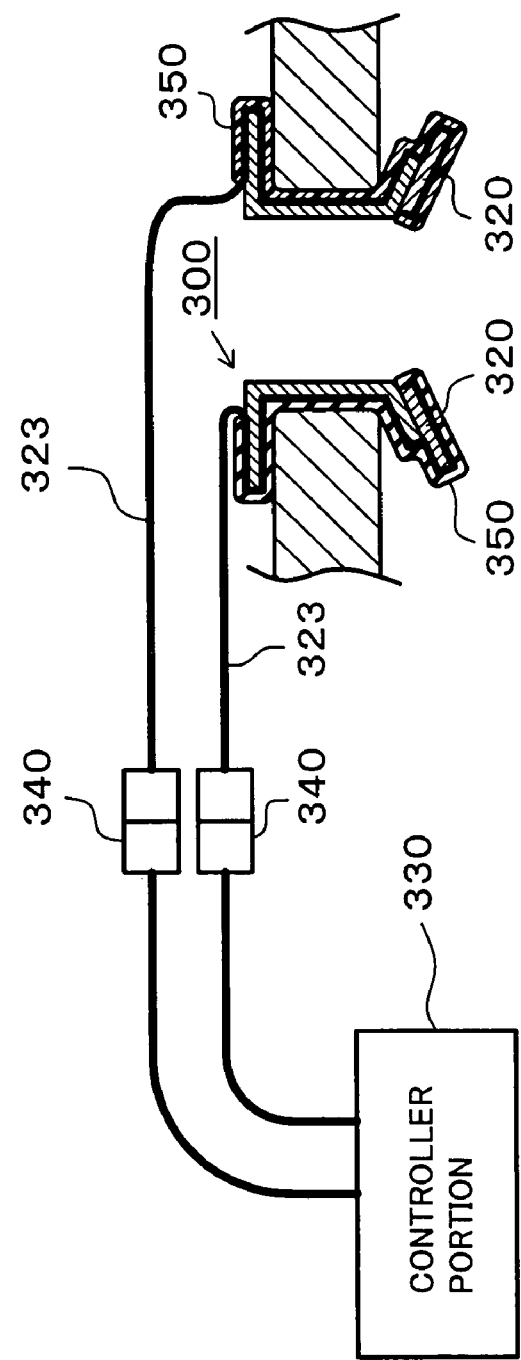
FIG. 15 is a block diagram showing one wiring example of the retractor of FIG. 8.

FIG. 15 shows one example of a connection for providing electric power to the lighting apparatus 320 of the retractor 300. The lighting apparatus 320 is connected to a controller portion 330 by the cords 323, and drives the light emitting elements, such as LED chips with electric power provided from the controller portion 330. The cord 323 is drawn out to the U-shaped opening portion side of each of the blades 315 and 316, as shown in FIG. 8, and extends to the side of the controller portion 330. A connector 340 is provided in the middle of the cord 323. The connector 340 can separate the lighting apparatus 320 from the controller portion 330. Thus, the lighting apparatus 320 side is disposable. The controller portion 330 can be commonly used.

The controller portion 330 has a power circuit, which receives electric power from the commercial power supply, the battery, or the like, and converts it into a current, voltage, or the like, for driving the lighting apparatus 320. In the example of FIG. 15, two power circuits are provided to drive two power supply devices attached to the pair of blades 315 and 316 of the retractor 300, respectively. The power circuit adjusts electric power for driving the lighting apparatus 320. In this case, in order to adjust the output of the LED, a PAM system, which provides variable current value of drive current, is employed. A PWM system which adjusts the duty ratio of current pulse, a system which can vary the number of the pulses with fixed width, and so on can be employed. However, it is necessary to take into consideration of noise generation in the medical field; therefore, the PAM system is more preferable.

When the commercial power supply is used, the power circuit converts AC power supply into DC power supply, and provides it to the LED. A portable battery, such as a primary battery or a rechargeable battery, can be used as a power supply. The battery can be attached to the belt of an operator or can be hung from his or her neck. In the case of short-time use, or in the case where a more compact battery is developed in the future, the battery can be installed in the outside of the arm portion of the retractor together with the dimmer. In this case, it is possible to make the equipment more compact.

The controller portion 330 may serves as a dimmer which can adjust the luminescence intensity of the LED by adjusting the current provided to the LED module 321. Alternatively, the lighting apparatus may have a dimmer provided separately from the controller portion. Irradiation of arbitrary illuminance is performed on the operation area with such dimming function. In the case where LEDs with different colors including an ultraviolet LED or the like are provided, it is preferable that the intensity of each color can be adjusted. For example, in the case where three colors, RGB of LEDs are used, the dimmer which individually controls the luminescence intensity of each color, thus, the luminescent color can be arbitrarily adjusted in use. Accordingly, it is possible to easily vary the illuminance or the tone of lighting depending on irradiation subjects, such as the tissue inside the patient's body, organs, or the like. The luminescent color is varied in an operation, thus, it is possible to increase the color difference of two parts whose color difference is small. Therefore, they can be clearly identified.

The LED is connected to the dimmer and the power supply with the cord 323. An electrical signal line such as a lead wire can be used as the cord 323. Generally, a cable used for lighting with a conventional optical fiber is thick, and its permissible bend angle is limited. Accordingly, there are problems in that handling is inconvenient and attention for adherence of stain to the connector part is necessary. On the contrary, the cord for electrical signal used in this embodiment is thin in comparison with the optical fiber, and has flexibility. In addition, it can be easily extended. Accordingly, there are advantages in that handling is easy and it is less prone to disturbing the operation. The cord 323 is preferably fastened to the blade to prevent entanglement or from being caught. In the example of FIG. 8, the cords 323 are fastened inside of the blades 315 and 316. It is more preferable that patterning wires are formed above the surface of the retractor through an insulating layer for providing electric power to the LED. A protection layer of insulator overlays the above patterning wires. The cord 323 or the patterning wires are fixed or formed on the surface of the blade of the retractor in the side that is not in direct contact with the tissue inside the patient's body.

In the example shown in FIG. 15, the controller portion 330 is connected to the cord 323 of the lighting apparatus 320 through the connector 340. The lighting apparatus 320 is detachable by the connector 340, and can be separated from the controller portion 330 at the connector 340 part, and thus is disposable. Accordingly, the cord part, which connects the connector 340 and the lighting apparatus 320, is disposable. It is possible to further improve safety. In the example of FIG. 15, a pair of lighting apparatuses 320 is connected to one controller portion 330. Needless to say, the controller portion can be individually provided for each lighting apparatus. The cord 323 is wired for each lighting apparatus 320 in the example of FIG. 15, but one connector can provide an integral connection for a plurality of lighting apparatuses.

Different types of lighting apparatuses can be connected to one controller portion. In this construction, in the case where drive electric power conditions are different depending on lighting apparatuses, for example, drive currents of LED chips provided in the lighting apparatus are different, illuminance values may become different due to the difference of drive electric power conditions, if they are connected to one controller portion without measures. Accordingly, a control circuit is provided in the lighting apparatus side, and a communication circuit is provided in the controller portion side, so that these can communicate with each other. The control circuit transmits drive electric power to the communication circuit depending on the type, the number and the connection forms, or the like, of LED chips to be used, and thus, the lighting apparatus can receive suitable electric power supply from the power circuit of the controller portion. Therefore, it is possible to maintain constant illuminance irrespective of the types of the lighting apparatuses connected thereto. The control circuit is composed of an IC and so on, and has a storage element, which stores the drive electric power conditions of the lighting apparatuses, such as ROM. In this case, the drive electric power conditions are set in consideration of deviations of elements of LED chips used for the lighting apparatus. Accordingly, it is possible to provide more accurate color adjustment. The control circuit is provided in a part that is different from the plate, in order to prevent the heat generated from the circuit from being thermally conducted to a part to be operated on. For example, it can be provided in the connector part or in the middle of the cord. Needless to say, the output power in the controller portion side may be manually continuously variable depending on the lighting apparatus, or a controller portion used only for each lighting apparatus may be prepared.

According to the embodiments of the present invention, it is possible to adjust the luminescent color depending on the individual difference. For example, when medical workers, such as doctors and nurses, become old, generally their eyesight and color discrimination deteriorate. In consideration of deterioration of discrimination due to age, lighting for easier color discrimination can be obtained by adjusting wavelength and brightness depending on the user.

Such adjustment is not limited to age. For example, it is known that there is a difference of visual senses between the Mongoloid race and the Caucasoid race. In consideration of racial difference, the color temperature can be adjusted so as to provide optimal color discrimination. As mentioned above, conditions can be optimized depending on the characteristics of the user.

The adjusted setting can be saved, and thus can be reused by loading the setting. Accordingly, it is possible to save time and effort by eliminating readjustment, and to provide a lighting apparatus with ease of operation. In addition, lighting conditions can be changed for illumination. Lighting conditions can be manually or automatically changed. When lighting conditions are automatically changed, the condition of low color temperature, the condition suitable for color discrimination of nervous, and the condition suitable for color discrimination of organs are alternately changed at a predetermined time interval, for example. Accordingly, it is possible to sharply and easily identify parts without changing conditions point by point during an operation or the like. When manually changed, lighting conditions are changed by a foot switch in a toggle manner. Particularly, this can improve convenience in medical applications, such as in an operation.

The lighting apparatus 320 is arranged and fixed at the position and angle so as to illuminate a retracted part which is incised by the retractor 300. In the example shown in the figures, the lighting apparatus 320 was secured to the retractor 300. Needless to say, the lighting apparatus 320 may be attached to a part other than the blade as long as it can illuminate a retracted part. The present invention is applied to the retractor for chest surgery in the description according to the example of FIG. 8, but can be applied to various types, such as a Jansen retractor and a Nagoya University type retractor. In addition, the present invention is not limited to application to a retractor for chest surgery, but can be applied to retractors used for other various parts. Furthermore, the aforementioned lighting apparatus is not limited to application to a retractor, but can be applied also to a thoracotomy device. The lighting apparatus refers to an apparatus including a lighting circuit attached to a retractor or the like, a retractor with such a lighting circuit attached thereto, and so on.

The lighting apparatus and filter apparatus of the present invention can be preferably used as a light source, which can be used as a shadowless lamp, or a filter to be combined with an illumination light source, for example. The present invention can be applied to a filter used to cover the above light source, goggles or goggles with light, which a medical worker wears, or goggles light, a retractor, and so on. In an apparatus which can acquire and display a medical image, such as an endoscope, the image display apparatus can be used as an enhancer, an image filter circuit, or the like, which improves contrast so as to sharply identify living body tissues in the displayed image.

As this invention may be embodied in several forms without departing from the spirit or essential characteristics thereof, the present embodiment is therefore illustrative and not restrictive, since the scope of the invention is defined by the appended claims rather than by the description preceding them, and all changes that fall within the metes and bounds of the claims or equivalence of such metes and bounds thereof are therefore intended to be embraced by the claims. This application is based on applications No. 2004-63181 filed in Japan on Mar. 5, 2004, the content of which is incorporated hereinto by reference.

What is claimed is:

1. A lighting apparatus capable of emitting white light, the lighting apparatus comprising:
    a module capable of emitting output light;
    a cord; and
    a controller portion connected to the module via the cord to supply electric power for driving the light emitting elements,
    wherein the module comprises:
    a first light emitting diode for emitting blue or bluish green light having a peak wavelength in a range of 480 nm to 510 nm; and
    a second light emitting diode for emitting red light having a peak wavelength in a range of 610 nm to 670 nm,
    wherein the controller portion controls electric current so as to output the light in which a range of wavelength 525 nm to 590 nm of a partial output light is not greater than $\frac{1}{5}$ of the partial light output in a range of wavelength 380 nm to 780 nm corresponding to visible light components, and
    wherein the peak of the first light emitting diode is substantially greater than that of the second light emitting diode.

2. The lighting apparatus according to claim 1, wherein a green light component included in the output light has a peak in a range of wavelength 520 to 590 nm, its spectral half-value width is not greater than 70 nm, and the light amount of at least the green light component can be independently adjusted.

3. The lighting apparatus according to claim 1, wherein the first light emitting means comprises an LED configured and arranged so that its light output can be independently adjusted.

4. The lighting apparatus according to claim 3, wherein the LED includes a wavelength conversion member.

5. The lighting apparatus according to claim 4, wherein the wavelength conversion member is a filter.

6. The lighting apparatus according to claim 4, wherein the wavelength conversion member is a phosphor.

7. A retractor having a lighting apparatus according to claim 1.

8. An endoscope having a lighting apparatus according to claim 1.

9. The lighting apparatus according to claim 1, wherein the first and second light emitting diodes do not include a liquid or gel.

10. A lighting apparatus capable of emitting white light, the lighting apparatus comprising:
- a module capable of emitting output light;
- a cord; and
- a controller portion connected to the module via the cord to supply electric power for driving the light emitting elements,
- wherein the module comprises:
- a first light emitting diode for emitting blue or bluish green light having a peak wavelength in a range of 480 nm to 510 nm; and
- a second light emitting diode for capable of emitting red light having a peak wavelength in a range of 610 nm to 670 nm,
- wherein the controller is capable of controlling electric current so as to output the light of which a range of wavelength 525 nm to 590 nm of a partial output light is not greater than 1/10 of the partial light output in a range of wavelength 380 nm to 780 nm corresponding to visible light components, and
- wherein the peak of the first list emitting diode is substantially greater than that of the second light emitting diode.

11. A lighting apparatus capable of emitting white light, the lighting apparatus comprising:
- a module capable of emitting output light;
- a cord; and
- a controller portion connected to the module via the cord to supply electric power for driving the light emitting elements,
- wherein the module comprises:
- a first light emitting diode for emitting blue or bluish green light having a peak wavelength in a range of 480 nm to 510 nm;
- a second light emitting diode for emitting red light having a peak wavelength in a range of 610 nm to 670 nm; and
- a third light emitting diode for emitting green light having a peak wavelength in a range of 520 nm to 590 nm,
- wherein spectral half-value width of the green light is not greater than 70 nm, and the light amount of at least the green light component is independently adjustable, and
- wherein the peak of the first light emitting diode is substantially greater than that of the second light emitting diode.

12. The lighting apparatus according to claim 11, wherein the apparatus can emit light containing only the green light component.

* * * * *